(12) United States Patent
Geroy et al.

(10) Patent No.: US 8,560,084 B2
(45) Date of Patent: Oct. 15, 2013

(54) LEAD BODY WITH INNER AND OUTER CO-AXIAL COILS

(75) Inventors: Jesse Geroy, Ham Lake, MN (US); John Swoyer, Andover, MN (US)

(73) Assignee: Greatbatch Ltd., Clarence, NY (US)

( * ) Notice: Subject to any disclaimer, the term of this patent is extended or adjusted under 35 U.S.C. 154(b) by 132 days.

(21) Appl. No.: 13/220,913

(22) Filed: Aug. 30, 2011

(65) Prior Publication Data

US 2013/0053864 A1    Feb. 28, 2013

(51) Int. Cl.
*A61N 1/05*     (2006.01)
(52) U.S. Cl.
USPC ............ 607/116; 607/1; 607/2; 607/115; 607/118; 600/372; 600/373; 600/377; 606/129
(58) Field of Classification Search
USPC .......... 607/1–2, 115–116, 118; 600/372–373, 600/377; 606/129
See application file for complete search history.

(56) References Cited

U.S. PATENT DOCUMENTS

| | | | |
|---|---|---|---|
| 4,640,983 A | 2/1987 | Comte | |
| 4,945,342 A * | 7/1990 | Steinemann | 174/113 R |
| 4,964,414 A | 10/1990 | Handa et al. | |
| 5,330,521 A | 7/1994 | Cohen | |
| 5,483,022 A | 1/1996 | Mar | |
| 6,295,476 B1 | 9/2001 | Schaenzer | |
| 6,456,888 B1 | 9/2002 | Skinner et al. | |
| 6,671,554 B2 | 12/2003 | Gibson et al. | |
| 6,920,361 B2 | 7/2005 | Williams | |
| 6,978,185 B2 | 12/2005 | Osypka | |
| 2003/0050680 A1 | 3/2003 | Gibson et al. | |
| 2004/0078070 A1 | 4/2004 | Baudino | |
| 2006/0089697 A1 | 4/2006 | Cross, Jr., et al. | |
| 2006/0200216 A1 | 9/2006 | Calzada et al. | |
| 2006/0229693 A1 | 10/2006 | Bauer et al. | |
| 2007/0179577 A1 | 8/2007 | Marshall et al. | |

* cited by examiner

*Primary Examiner* — Deborah Malamud
(74) *Attorney, Agent, or Firm* — Michael P. Horvath (57) ABSTRACT

A biomedical conductor assembly adapted for at least partial insertion in a living body. The conductor assembly includes a plurality of the first electrical conductors each covered with an insulator and helically wound in a first direction to form an inner coil with a lumen. A plurality of second electrical conductors each including a plurality of un-insulated wires twisted in a ropelike configuration around a central axis to form a plurality of cables. Each cable is covered with an insulator and helically wound in a second opposite direction forming an outer coil in direct physical contact with the inner coil. The inner and outer coils are covered by an insulator. A method of making the conductor assembly and implanting a neurostimulation system is also disclosed.

20 Claims, 10 Drawing Sheets

Fig. 9

LEAD BODY WITH INNER AND OUTER CO-AXIAL COILS

FIELD

The present disclosure relates to a lead body with inner and outer co-axial coils each having a plurality of discrete electrical paths. The inner and outer coils are in direct physical contact and coiled in opposite directions.

BACKGROUND

The human body imposes stringent requirements on electrical conductors that are implanted in it. Leads inserted in a living body that form a part of a stimulation and/or measuring device are subjected to almost continuous flexure during body movement. Also, a living body constitutes a site that is chemically and biologically hostile to anything that invades it. Consequently, leads ideally have good deformability, particularly bending ability, high fatigue resistance, corrosion resistance, and a high degree of electric conductance.

U.S. Pat. No. 4,640,983 (Comte) discloses a lead body having at least one spiral which is formed from at least one conductor. Each conductor consists of wires that are stranded together to form a bundle. The wires belonging to a conductor can all consist of the same material or of different materials, one of which has a large breaking strength and the other one having high electric conductivity. One embodiment discloses inner and outer coils wound in the same direction and separated by an insulating sheath.

U.S. Pat. No. 5,483,022 (Mar) discloses a lead body having at least one helical coil formed from at least one electrical cable. Each cable is formed from several wires twisted in a ropelike configuration. Each wire is a composite of a core of a highly conductive material and a coveting of a strong and biocompatible material, with all adjacent wires belonging to the same cable in un-insulated contact with each other. One embodiment discloses inner and outer coils wound in the same direction and separated by an insulating sheath.

U.S. Pat. No. 6,978,185 (Osypka) discloses a lead body having electrically active and inactive elements helically wound together. The active elements are separated from each other by the inactive elements. One embodiment discloses inner and outer coils wound in opposite directions and separated by an insulating sheath.

BRIEF SUMMARY

The present disclosure relates to a lead body with inner and outer co-axial coils each having a plurality of discrete electrical paths. The inner and outer coils are coiled in opposite directions and in direct physical contact with each other. Embodiments with twelve discrete electrical paths are disclosed. The conductor device provides a relatively high electric conductance with great flexibility, expandability, breaking strength and, in particular, fatigue resistance.

One embodiment is directed to a biomedical conductor assembly adapted for at least partial insertion in a living body. The conductor assembly includes a plurality of first and second electrical conductors each covered with an insulator. A plurality of the first electrical conductors are helically wound in a first direction to form an inner coil with a lumen and a plurality of the second electrical connectors helically wound in a second opposite direction forming an outer coil in direct physical contact with the inner coil. An insulator covers the inner and outer coils. The plurality of second electrical conductors each include a plurality of un-insulated wires twisted in a ropelike configuration around a central axis to form a plurality of cables. Each cable is covered with an insulator. The un-insulated wires are preferably movable with respect to each within the insulator.

The inner coil preferably slides relative to the outer coil within the conductor assembly. The first electrical conductors each optionally include a plurality of discrete insulated wires. The first electrical conductors optionally include a plurality of un-insulated wires twisted in a ropelike configuration around a central axis to form a cable wherein each cable is covered with an insulator.

In one embodiment, the un-insulated wires in the second electrical conductors include a core of a first material surrounded by a covering of a second material. In another embodiment, the second electrical conductors include a center wire and a plurality of un-insulated wires twisted in a ropelike configuration around the center wire. The center wire preferably has a greater breaking strength than the un-insulated wires.

The conductor assembly can include any number of discrete conductors. In one embodiment, the inner coil includes four discrete insulated wires and the outer coil includes four or eight discrete insulated cables.

In another embodiment is directed to a biomedical conductor assembly adapted for at least partial insertion in a living body. The conductor assembly includes a plurality of the first electrical conductors each covered with an insulator and helically wound in a first direction to form an inner coil with a lumen. A plurality of second electrical conductors wound in a second opposite direction forming an outer coil in direct physical contact with the inner coil. The second electrical conductors each including a plurality of un-insulated wires twisted in a ropelike configuration around a central axis to form a plurality of cables covered with an insulator. The inner and outer coils are covered by an insulator.

The present disclosure is also directed to a therapy delivery element including an elongated lead body having a proximal end and a distal end. The lead body includes a plurality of the first electrical conductors each covered with an insulator and helically wound in a first direction to form an inner coil with a lumen and a plurality of second electrical conductors each including a plurality of un-insulated wires twisted in a ropelike configuration around a central axis to form a plurality of cables. Each cable is covered with an insulator and helically wound in a second opposite direction forming an outer coil in direct physical contact with the inner coil. An insulator covers the inner and outer coils. At least one electrically conductive connector is operatively associated with the proximal end of the lead body and at least one electrode is operatively associated with the distal end of the lead body. Each matched set of connectors and electrodes are electrically coupled with one of the first or second electrical conductors.

The therapy delivery element preferably includes a stylet wire having a distal end inserted into the lumen through an opening at the proximal end of the lead body and a proximal end attached to a stylet handle.

The present disclosure is also directed to a neurostimulation system including an implantable pulse generator and a therapy delivery element in accordance with an embodiment of the present disclosure. A stylet wire having a distal end is inserted into the lumen through an opening at the proximal end of the lead body and a proximal end attached to a stylet handle.

The present disclosure is also directed to a method of making a therapy delivery element adapted for at least partial insertion in a living body. The method includes helically winding a plurality of the first electrical conductors each covered with an insulator in a first direction to form an inner coil with a lumen. A plurality of second electrical conductors is helically wound in a second opposite direction forming an outer coil in direct physical contact with the inner coil. Each of the second electrical conductors includes a plurality of un-insulated wires twisted in a ropelike configuration around a central axis to form a plurality of cables covered with an insulator. An insulating covering is applied to the inner and outer coils to form a lead body. At least one electrically conductive connector is attached to a proximal end of the lead body and at least one electrode is attached to a distal end of the lead body. Each matched set of connectors and electrodes are electrically coupled with one of the first or second electrical conductors.

The present disclosure is also directed to a method of implanting a neurostimulation system. The method includes grasping a stylet handle attached to a stylet wire inserted into a lumen of a therapy delivery element in accordance with an embodiment of the present disclosure. The electrodes at a distal end of a therapy delivery element are steered to a target location within the living body. The stylet is removed from the therapy delivery element. An implantable pulse generator is implanted within the living body. The electrical contacts at the proximal end of the therapy delivery element are electrically coupled with the implantable pulse generator.

DETAILED DESCRIPTION OF SOME EMBODIMENTS

The description that follows relates to spinal cord stimulation (SCS) system. However, it is to be understood that the while the present disclosure lends itself well to applications in SCS, the disclosure in its broadest aspects may not be so limited. Rather, the disclosure may be used with any type of implantable therapy delivery system with one or more therapy delivery elements. For example, the present disclosure may be used as part of a pacemaker, a defibrillator, a cochlear stimulator, a retinal stimulator, a stimulator configured to produce coordinated limb movement, a cortical stimulator, a deep brain stimulator, peripheral nerve stimulator, microstimulator, or in any other neural stimulator configured to treat urinary incontinence, sleep apnea, shoulder sublaxation, headache, etc.

In another embodiment, one or more of the therapy delivery elements may be a fluid delivery conduit, such as a catheter, including an inner lumen that is placed to deliver a fluid, such as pharmaceutical agents, insulin, pain relieving agents, gene therapy agents, or the like from a fluid delivery device (e.g., a fluid reservoir and/or pump) to a respective target tissue site in a patient.

In yet another embodiment, one or more of the therapy delivery elements may be an electrical lead including one or more sensing electrodes to sense physiological parameters (e.g., blood pressure, temperature, cardiac activity, etc.) at a target tissue site within a patient. In the various embodiments contemplated by this disclosure, therapy may include stimulation therapy, sensing or monitoring of one or more physiological parameters, fluid delivery, and the like. "Therapy delivery element" includes pacing or defibrillation leads, stimulation leads, sensing leads, fluid delivery conduit, and any combination thereof "Target tissue site" refers generally to the target site for implantation of a therapy delivery element, regardless of the type of therapy.

Figure 1:
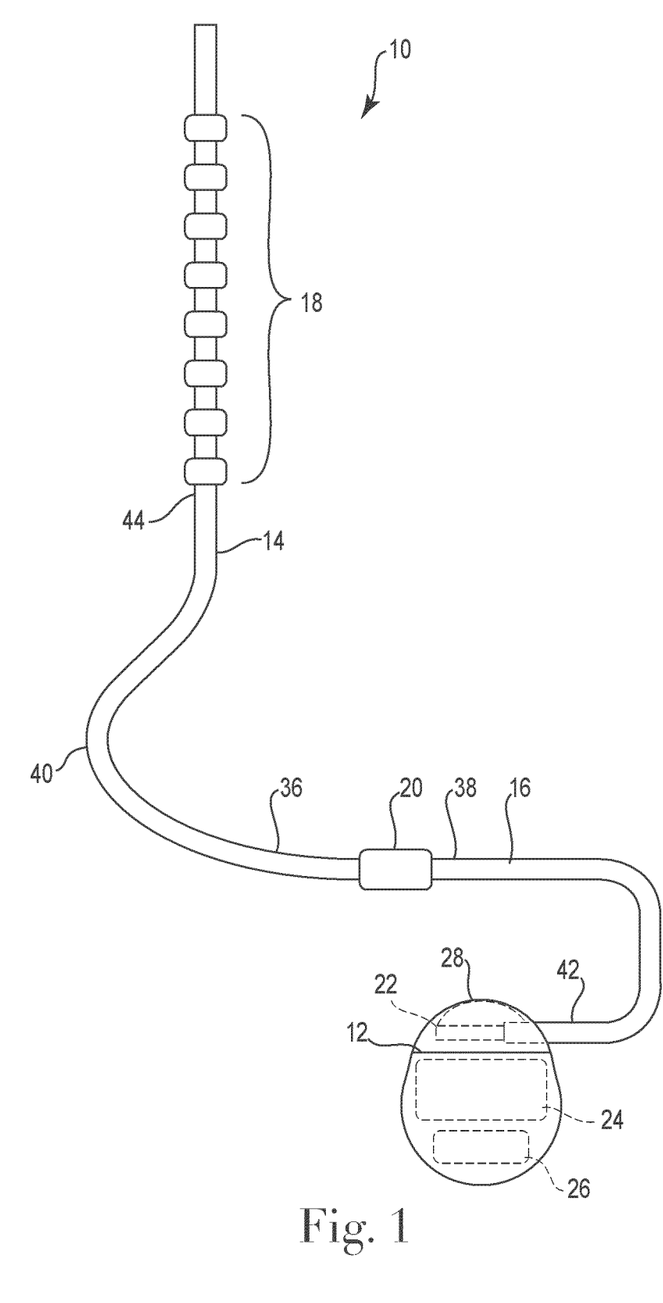
FIG. 1 is a schematic illustration of a therapy delivery system.

FIG. 1 illustrates a generalized therapy delivery system 10 that may be used in spinal cord stimulation (SCS), as well as other stimulation applications. The therapy delivery system 10 generally includes an implantable pulse generator 12 ("IPG") ("IPG"), an implantable therapy delivery element 14, which carries an array of electrodes 18 (shown exaggerated for purposes of illustration), and an optional implantable extension lead 16. Although only one therapy delivery element 14 is shown, typically two or more therapy delivery elements 14 are used with the therapy delivery system 10.

The therapy delivery element 14 includes lead body 40 having a proximal end 36 and a distal end 44. The lead body 40 typically has a diameter of between about 0.03 inches to 0.07 inches and a length within the range of 30 cm to 90 cm for spinal cord stimulation applications. The lead body 40 may include a suitable electrically insulative costing, such as, a polymer (e.g., polyurethane or silicone).

In the illustrated embodiment, proximal end 36 of the therapy delivery element 14 is electrically coupled to distal end 38 of the extension lead 16 via a connector 20, typically associated with the extension lead 16. Proximal end 42 of the extension lead 16 is electrically coupled to the implantable pulse generator 12 via connector 22 associated with housing 28. Alternatively, the proximal end 36 of the therapy delivery element 14 can be electrically coupled directly to the connector 22.

In the illustrated embodiment, the implantable pulse generator 12 includes electronic subassembly 24 (shown schematically), which includes control and pulse generation circuitry (not shown) for delivering electrical stimulation energy to the electrodes 18 of the therapy delivery element 14 in a controlled manner, and a power supply, such as battery 26.

The implantable pulse generator 12 provides a programmable stimulation signal (e.g., in the form of electrical pulses or substantially continuous-time signals) that is delivered to target stimulation sites by electrodes 18. In applications with more than one therapy delivery element 14, the implantable pulse generator 12 may provide the same or a different signal to the electrodes 18.

Alternatively, the implantable pulse generator 12 can take the form of an implantable receiver-stimulator in which the power source for powering the implanted receiver, as well as control circuitry to command the receiver-stimulator, are contained in an external controller inductively coupled to the receiver-stimulator via an electromagnetic link. In another embodiment, the implantable pulse generator 12 can take the form of an external trial stimulator (ETS), which has similar pulse generation circuitry as an IPG, but differs in that it is a non-implantable device that is used on a trial basis after the therapy delivery element 14 has been implanted and prior to implantation of the IPG, to test the responsiveness of the stimulation that is to be provided.

The housing 28 is composed of a biocompatible material, such as for example titanium, and forms a hermetically sealed compartment containing the electronic subassembly 24 and battery 26 protected from the body tissue and fluids. The connector 22 is disposed in a portion of the housing 28 that is, at least initially, not sealed. The connector 22 carries a plurality of contacts that electrically couple with respective terminals at proximal ends of the therapy delivery element 14 or extension lead 16. Electrical conductors extend from the connector 22 and connect to the electronic subassembly 24.

Figure 2:
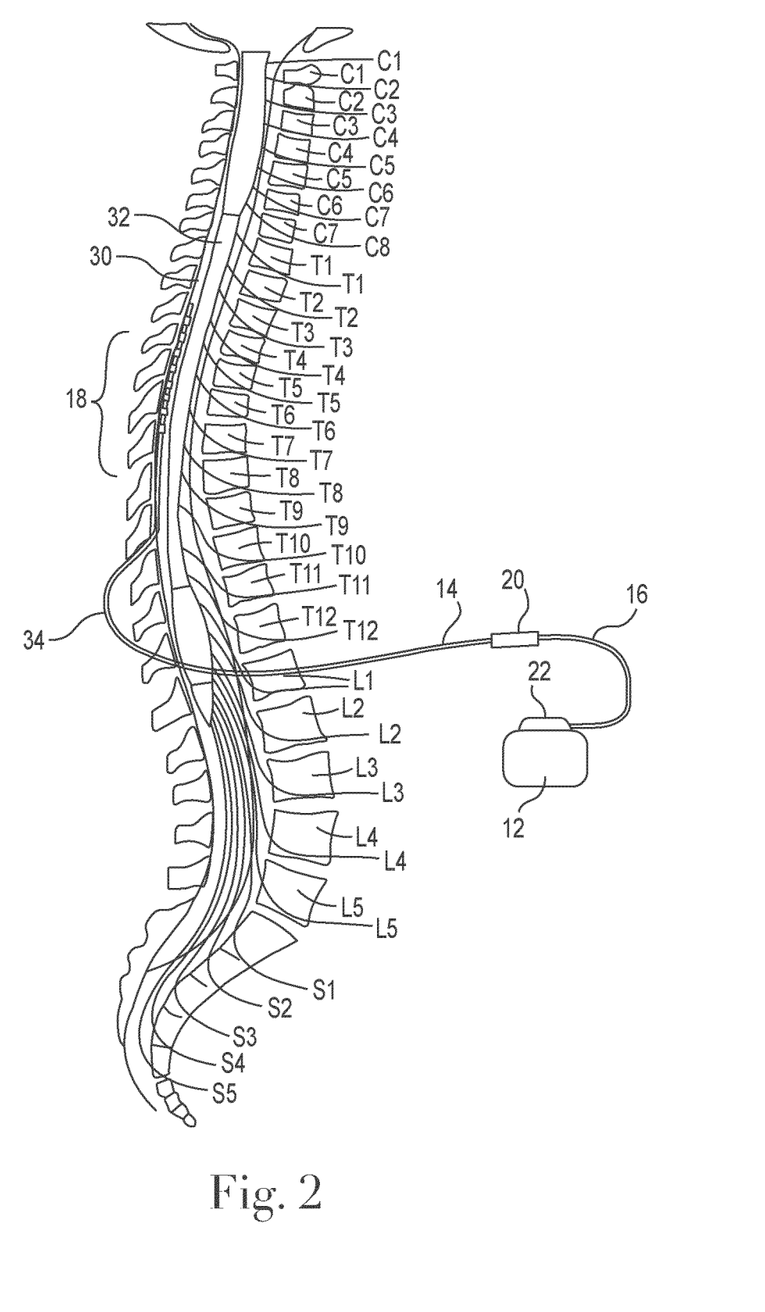
FIG. 2 is a schematic illustration of an environment for a therapy delivery system in accordance with an embodiment of the present disclosure.

FIG. 2 illustrates the therapy delivery element 14 implanted in the epidural space 30 of a patient in close proximity to the dura, the outer layer that surrounds the spinal cord 32, to deliver the intended therapeutic effects of spinal cord electrical stimulation. The target stimulation sites may be anywhere along the spinal cord 32, such as for example proximate the sacral nerves.

Figure 3:
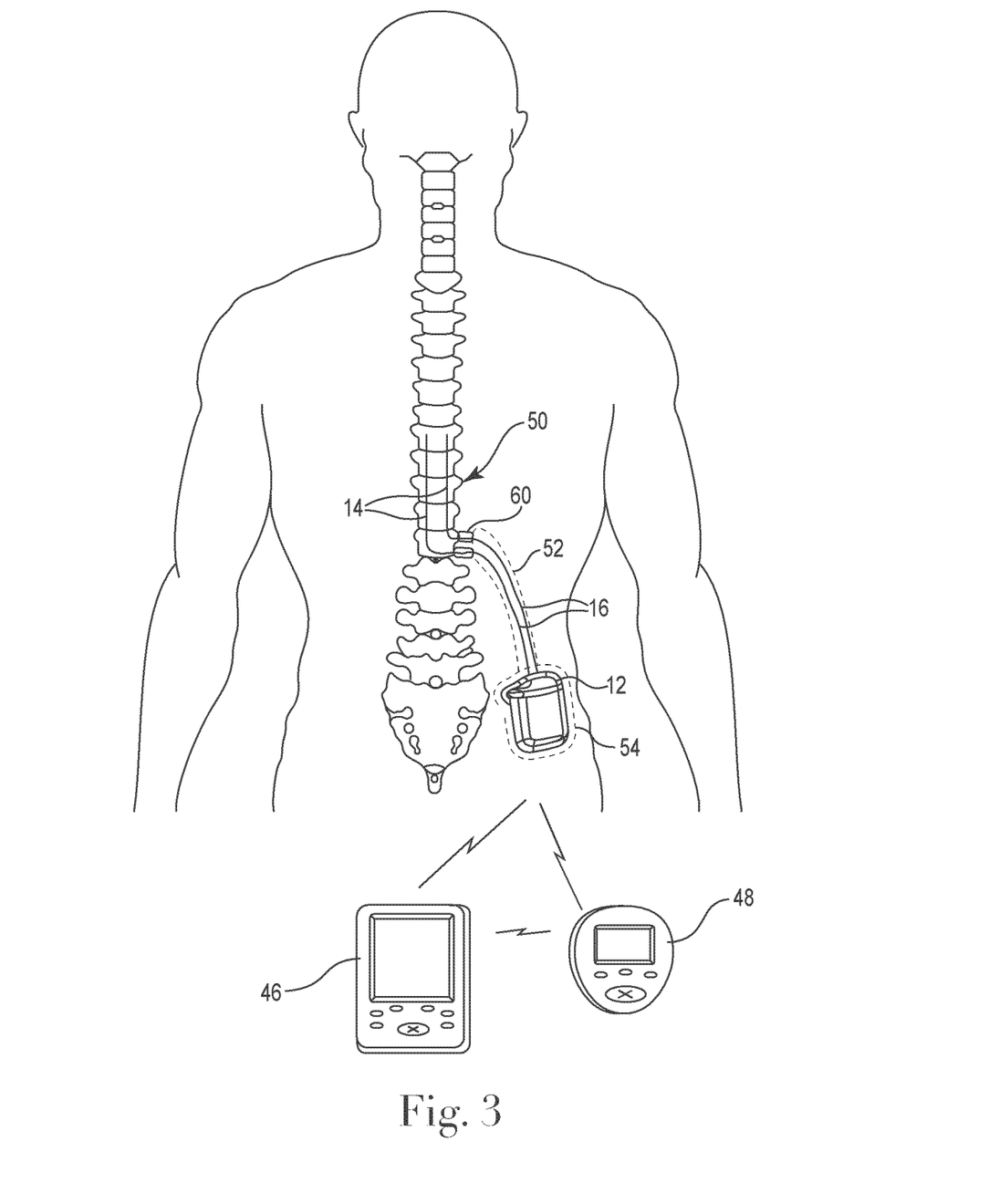
FIG. 3 is an alternate illustration of the environment for an implantable pulse generator with a therapy delivery element in accordance with an embodiment of the present disclosure.

Because of the lack of space near the lead exit point 34 where the therapy delivery element 14 exits the spinal column, the implantable pulse generator 12 is generally implanted in a surgically-made pocket either in the abdomen or above the buttocks, such as illustrated in FIG. 3. The implantable pulse generator 12 may, of course, also be implanted in other locations of the patient's body. Use of the extension lead 16 facilitates locating the implantable pulse generator 12 away from the lead exit point 34. In some embodiments, the extension lead 16 serves as a lead adapter if the proximal end 36 of the therapy delivery element 14 is not compatible with the connector 22 of the implantable pulse generator 12, since different manufacturers use different connectors at the ends of their stimulation leads and are not always compatible with the connector 22.

As illustrated in FIG. 3, the therapy delivery system 10 also may include a clinician programmer 46 and a patient programmer 48. Clinician programmer 46 may be a handheld computing device that permits a clinician to program neurostimulation therapy for patient using input keys and a display. For example, using clinician programmer 46, the clinician may specify neurostimulation parameters for use in delivery of neurostimulation therapy. Clinician programmer 46 supports telemetry (e.g., radio frequency telemetry) with the implantable pulse generator 12 to download neurostimulation parameters and, optionally, upload operational or physiological data stored by implantable pulse generator 12. In this manner, the clinician may periodically interrogate the implantable pulse generator 12 to evaluate efficacy and, if necessary, modify the stimulation parameters.

Similar to clinician programmer 46, patient programmer 48 may be a handheld computing device. Patient programmer 48 may also include a display and input keys to allow patient to interact with patient programmer 48 and the implantable pulse generator 12. The patient programmer 48 provides patient with an interface for control of neurostimulation therapy provided by the implantable pulse generator 12. For example, patient may use patient programmer 48 to start, stop or adjust neurostimulation therapy. In particular, patient programmer 48 may permit patient to adjust stimulation parameters such as duration, amplitude, pulse width and pulse rate, within an adjustment range specified by the clinician via clinician programmer 46, or select from a library of stored stimulation therapy programs.

The implantable pulse generator 12, clinician programmer 46, and patient programmer 48 may communicate via cables or a wireless communication. Clinician programmer 46 and patient programmer 48 may, for example, communicate via wireless communication with the implantable pulse generator 12 using RF telemetry techniques known in the art. Clinician programmer 46 and patient programmer 48 also may communicate with each other using any of a variety of local wireless communication techniques, such as RF communication according to the 802.11 or Bluetooth specification sets, infrared communication, e.g., according to the IrDA standard, or other standard or proprietary telemetry protocols.

FIG. 3 also illustrates a general environmental that may benefit from use of a tunneling tool in accordance with an embodiment of the present disclosure. Since the implantable pulse generator 12 is located remotely from target location 50 for therapy, the therapy delivery element 14 and/or the extension lead 16 is typically routed through a pathway 52 subcutaneously formed along the torso of the patient to a subcutaneous pocket 54 where the implantable pulse generator 12 is located. As used hereinafter, "lead" and "lead extension" are used interchangeably, unless content clearly dictates otherwise.

The therapy delivery elements 14 are typically fixed in place near the location selected by the clinician using the present suture anchors 60. The suture anchors 60 can be positioned on the therapy delivery element 14 in a wide variety of locations and orientations to accommodate individual anatomical differences and the preferences of the clinician. The suture anchors 60 may then be affixed to tissue using fasteners, such as for example, one or more sutures, staples, screws, or other fixation devices. The tissue to which the suture anchors 60 are affixed may include subcutaneous fascia layer, bone, or some other type of tissue. Securing the suture anchors 60 to tissue in this manner prevents or reduces the chance that the therapy delivery element 14 will become dislodged or will migrate in an undesired manner.

Figure 4A:
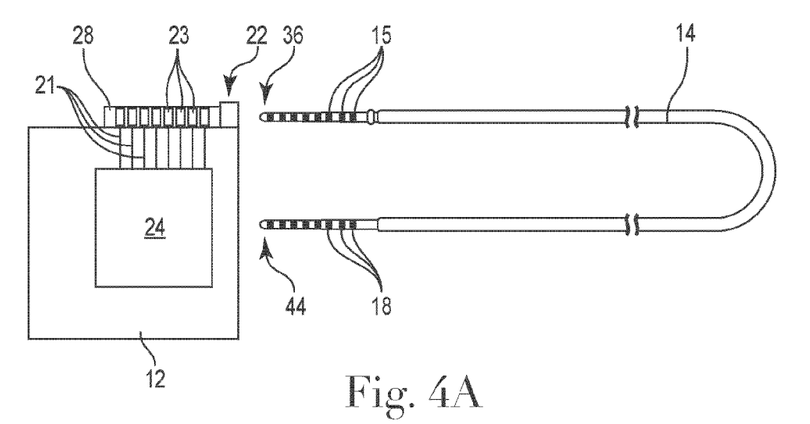
FIG. 4A is a schematic illustration of an implantable pulse generator and a therapy delivery element in accordance with an embodiment of the present disclosure.

FIG. 4A illustrates the therapy delivery element 14 including one or more electrical contacts 15 at the proximal end 36, and one or more electrodes 18 at the distal end 44. The contacts 15 and electrodes 18 are electrically coupled via insulated wires running through the therapy delivery element 14. Proximal end 36 of the therapy delivery element 14 is electrically and mechanically coupled to implantable pulse generator 12 by the connector assembly 22.

The connector assembly 22 includes a plurality of discrete contacts 23 located in the housing 28 that electrically couple contact rings 15 on the proximal end of the therapy delivery element 14. The discrete contacts 23 are electrically coupled to circuitry 24 in the implantable pulse generator 12 by conductive members 21. Each contact ring 15 is electrically coupled to one or more of the electrodes 18 located at the distal end 44 of the therapy delivery element 14. Consequently, the implantable pulse generator 12 can independently deliver electrical impulses to each of the electrodes 18.

Figure 4B:
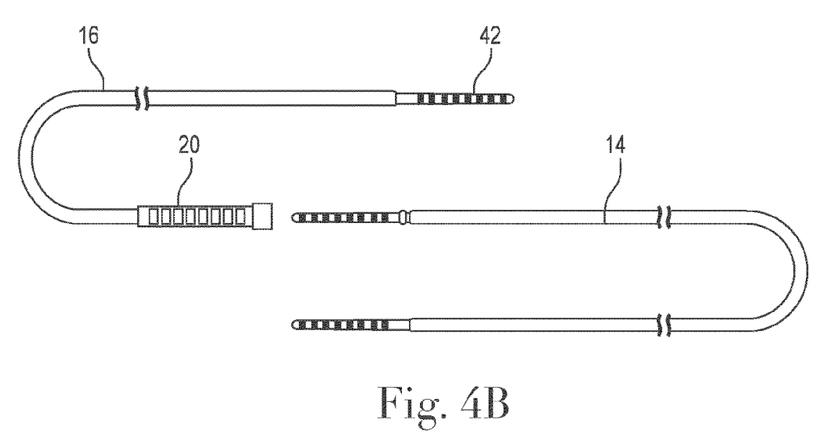
FIG. 4B is a schematic illustration of a lead extension and a therapy delivery element in accordance with an embodiment of the present disclosure.

Alternatively, the therapy delivery element 14 can be coupled to the implantable pulse generator 12 through one or more lead extensions 16, as illustrated in FIG. 4B. The connector 20 at the distal end 38 of the lead extension 16 preferably includes a plurality of the contacts 23 configured in a manner similar to the connector assembly 22.

Figure 5A:
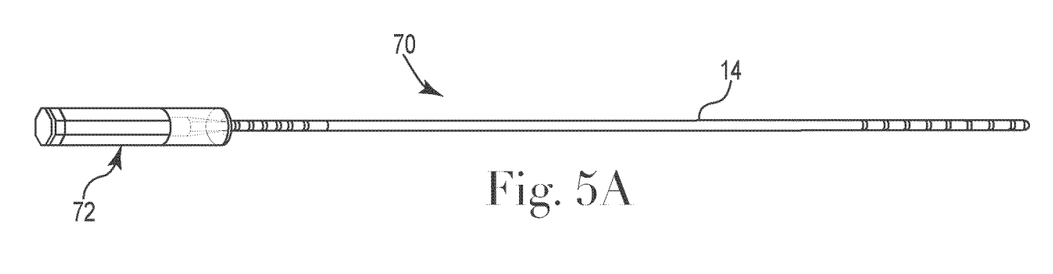
FIG. 5A is a schematic illustration of a stylet-lead assembly in accordance with an embodiment of the present disclosure.
Figure 5B:
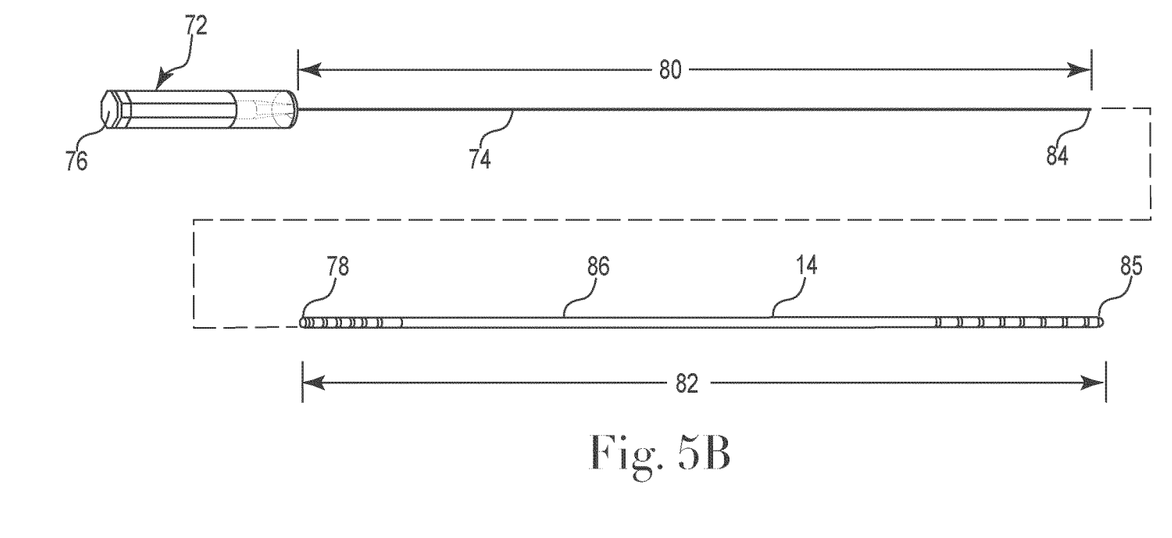
FIG. 5B is an exploded view of the stylet-lead assembly of FIG. 5A.

FIGS. 5A and 5B illustrate a stylet/lead assembly 70 including the therapy delivery element 14 in accordance with an embodiment of the present disclosure. The term stylet refers to a tool inserted into the lumen of a therapy delivery element, such as a neurostimulation lead, to stiffen the lead body and to facilitate its insertion into a target tissue.

In the illustrated embodiment, stylet 72 includes stylet wire 74 attached to handle 76. The stylet wire 74 has a diameter smaller than lumen 78 in the lead body 86 of the therapy delivery element 14. Length 80 is typically the same, or slightly greater than, length 82 of the lumen 78 so the distal end 84 of the stylet wire 74 preferably reaches distal end 85 of the therapy delivery element 14. The distal end 85 of the therapy delivery element is typically sealed, so the length 82 of the lumen 78 is less than the length of the therapy delivery element 14. In use, distal end 84 of the stylet wire 74 is inserted in lumen 78 of the therapy delivery element 14 to create the stylet/lead assembly 70.

Conventional stylet wires for the SCS application are typically made of stainless steel or tungsten. Super-elastic materials provide excellent kink resistance but have poor resistance to buckling forces and torque. Consequently, a stylet wire 74 made from these materials alone is not be suitable for use for SCS therapy delivery elements. Stylet wires manufactured from combinations of linear and super-elastic materials have been evaluated, as disclosed in U.S. Pat. Nos. 6,214,016; 6,168,571; 5,238,004; 6,270,496 and 5,957,966, which are hereby incorporated by reference.

Figure 6A:
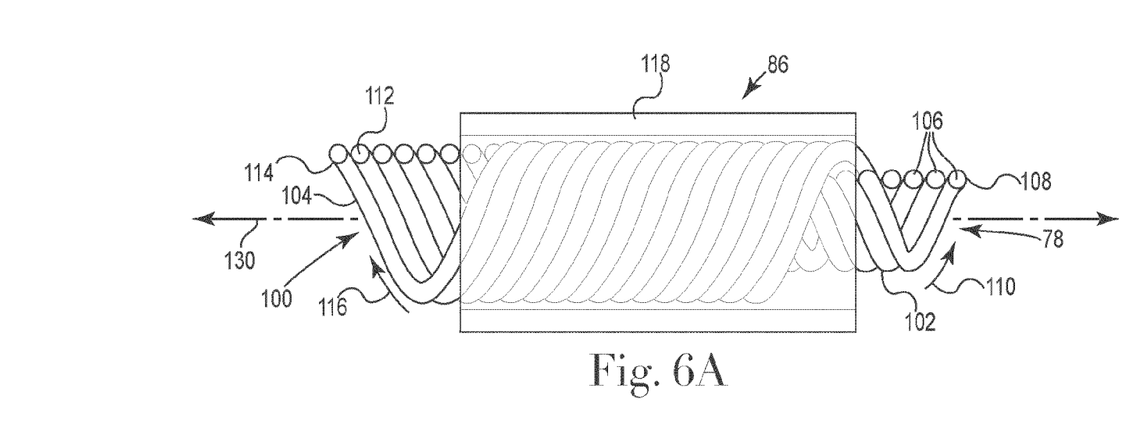
FIGS. 6A and 6B are sectional views of a lead body in accordance with an embodiment of the present disclosure.
Figure 6B:
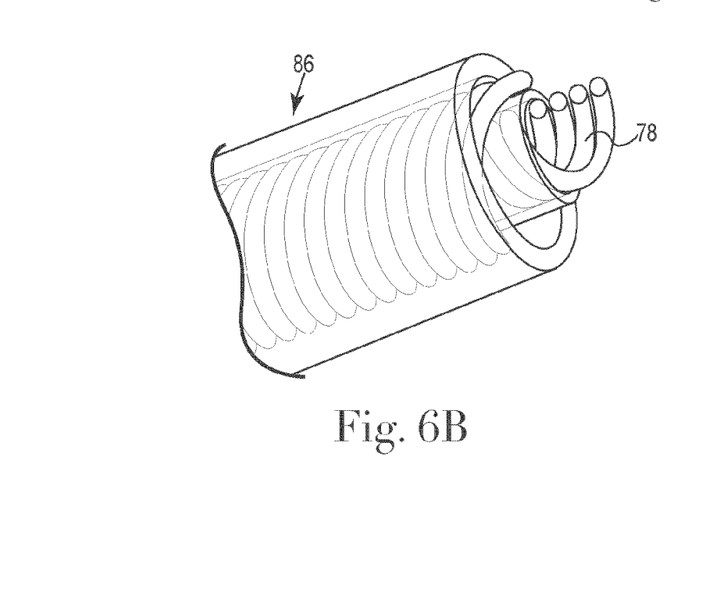

FIGS. 6A and 6B are cut-away views of a conductor assembly 100 for the lead body 86 having an inner coil 102 and outer coil 104 in accordance with an embodiment of the present disclosure. The inner coil 102 includes a plurality of discrete electrical conductors 106 each covered with an insulator 108 and helically wound in a first direction 110 around lumen 78 that receives stylet wire 74. The outer coil 104 includes a plurality of discrete electrical conductors 112 each covered with an insulator 114 and helically wound in a second opposite direction 116. The insulators 108, 114 provide electrical integrity between each electrical conductor 106, 112 in the conductor assembly 100. The pitch of the inner and outer coils 102, 104 can be the same or different.

Insulator 118 surrounds both the inner and outer coils 102, 104. The insulator 118 is preferably a rubber-elastic, bendable and biologically compatible material, such as for example, an elastomer on a polyurethane or silicon base.

The conductor assembly 100 preferably includes at least one electrical conductor 106, 112 for each electrode 18. In one embodiment, the inner and outer coils 102, 104 each include four electrical conductors 106, 112, to support an eight-electrode lead. In another embodiment, the inner coil 102 includes four electrical conductors 106 and the outer coil 104 includes eight electrical conductors 112, to support a twelve-electrode lead. Any number of electrical conductors 106, 112 can be used in the present conductor assembly 100 to provide the desired number of circuit paths for the electrodes.

The inner coil 102 is preferably in direct physical contact with the outer coil 104, reducing the size of the conductor assembly 100 and increasing the density of available circuit paths. Winding the electrical conductors 106, 112 in opposite directions 110, 116 permits movement of the inner coil 102 relative to the outer coil 104 and permits the conductor assembly 100 to be bent with such a small radius of curvature without permanent or lasting deformation. The inner and outer coils 102, 104 also permit the conductor assembly 100 to elastically expandable in longitudinal direction 130. Configuring the coils 102, 104 as opposing helical coils also enhances torque transfer by the lead body 86. The increased torque transfer aids during implantation of the therapy delivery element 14.

Figure 6C:
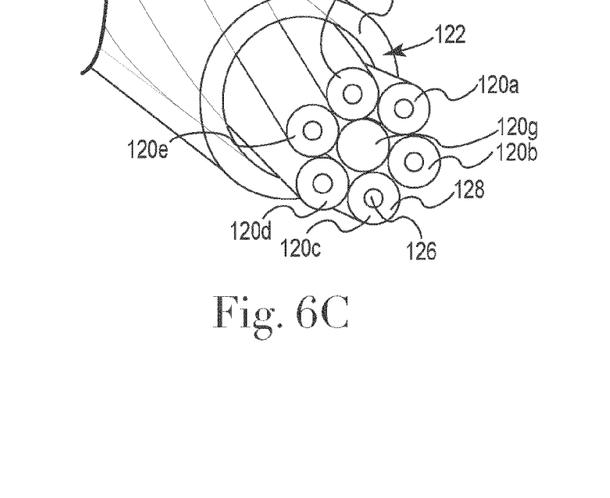
FIG. 6C is a sectional view of an electrical conductor including a plurality of un-insulated wires in accordance with an embodiment of the present disclosure.

The electrical conductors 106, 112 can include a single conductive element, a plurality of conductive wires, or a combination thereof. As illustrated in FIG. 6C, one or more of the electrical conductors 106, 112 optionally include a plurality of un-insulated conductive wires 120a-120g (collectively "120") twisted in a ropelike configuration 122. Insulator 124 surrounds the conductive wires 120 to form one of the electrical conductor 106, 112, also referred to a cable. The wires 120 are preferably not rigidly connected together, but rather, only contact one another and can move with respect to one another within certain limits.

In the illustrated embodiment, the six outer wires 120a-120f are uniformly distributed around the center wire 120g. The outer wires 120a-120f are preferably composites including a core 126 of a first material and a covering 128 of a second material. The core 126 preferably has greater electrical conductivity than the covering 128 and the covering 128 preferably has a greater breaking strength and better biocompatibility than the core 126. For example, the core 126 can be silver or copper and the covering 128 can be a nickel-cobalt-chromium-molybdenum alloy, such as for example, MP35N.

The center wire 120g is preferably constructed from a material with a greater breaking strength than the six outer wires 120a-120f. The center wire 120g can optionally be constructed from a non-conductive material, such as for example a monofilament. In one embodiment, the center wire 120g is constructed from the same material as the covering layer 128. Alternatively, the center wire 120g can be one of a variety of alloys, such as the CoNiCrMoWFe alloy (standard ASTM F 563-78) supplied under the commercial name Syntacoben by Institut Straumann AG, Switzerland; the CoCr-FeNi alloy supplied under the commercial name Elgiloy by Elgin National Watch Co., U.S.A.; stainless steel, such as the Fe, Cr, Ni, Mo containing steel (standards ISO 5832/1; ASTM F 138-76) commercially available under the designation 316 L; or a variety of other materials disclosed in U.S. Pat. No. 4,640,983 (Comte), which is hereby incorporated by reference.

Bending stress, or flexure stress, varies with position throughout the cross section of the wires 120. Stress is zero at the center of the wires 120, but increases with distance from the center. Since the maximum stress occurs at the surface of the wires 120, using a composite material with the strongest material on the covering 128 provides significant advantage by allowing greater stress without permanent deformation. Since minimal stress occurs in the core 126 of the wire 120, it is less important that the core material be strong.

Figure 7A:
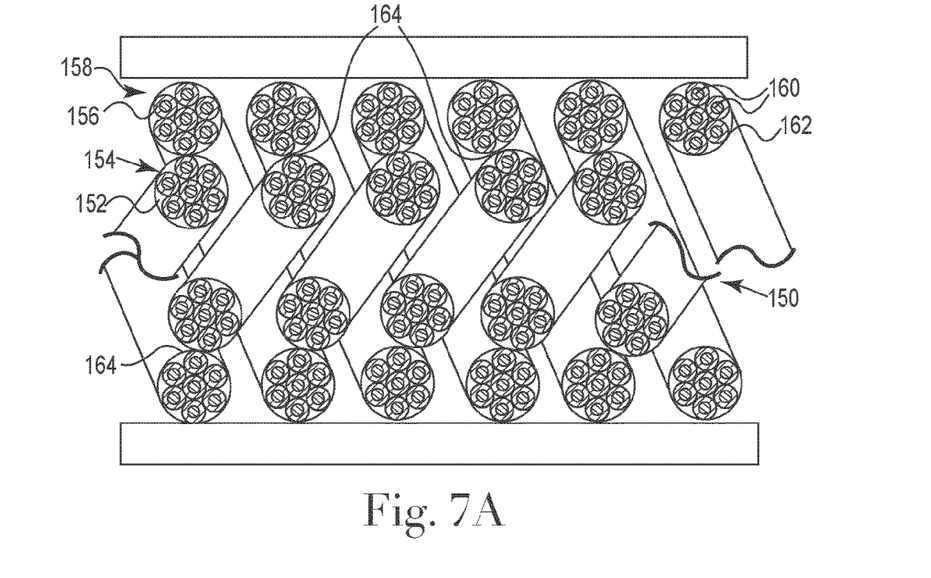
FIGS. 7A-7D are side sectional views of various conductor assemblies in accordance with an embodiment of the present disclosure.

FIG. 7A is a cross sectional view conductor assembly 150 in which the electrical conductors 152 for the inner coil 154 and the electrical conductors 156 for the outer coil 158 each include a plurality of un-insulated wires 160 surrounded by an insulating layer 162 in accordance with an embodiment of the present disclosure. The electrical conductors 152 in the inner coil 154 contact the electrical conductors 156 of the outer coil 158 at a plurality of interfaces 164.

Figure 7B:
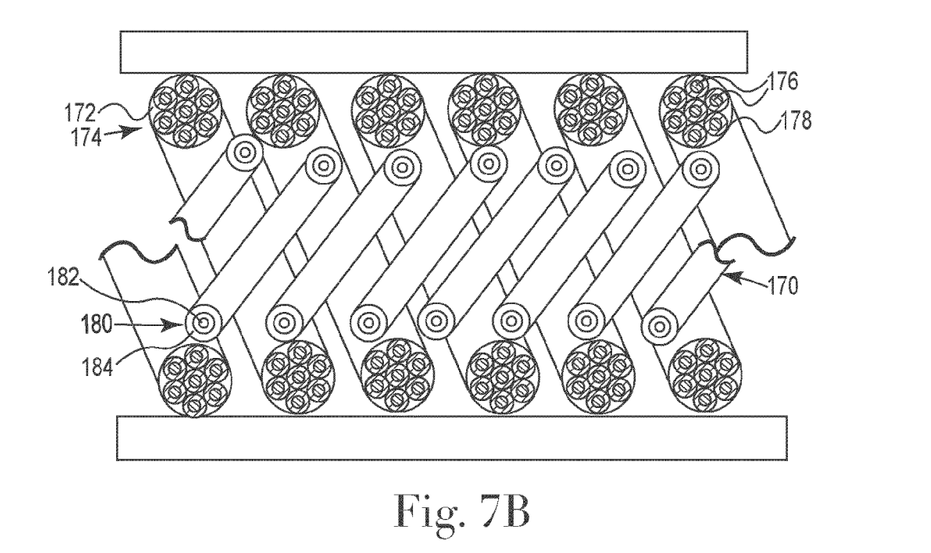

FIG. 7B is a cross sectional view conductor assembly 170 in which the electrical conductors 172 for the outer coil 174 each include a plurality of un-insulated wires 176 surrounded by an insulating layer 178, and the inner coil 180 includes a plurality of insulated electrical conductors 182 each with a single conductive element in accordance with an embodiment of the present disclosure. The electrical conductors 172 in the outer coil 174 contact the electrical conductors 182 of the inner coil 180 at a plurality of interfaces 184.

Figure 7C:
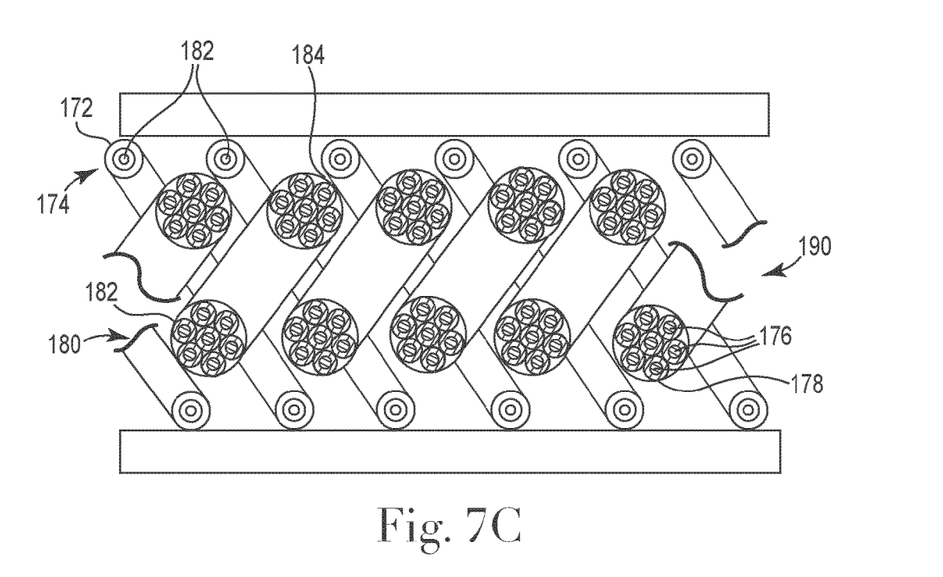
Figure 7D:
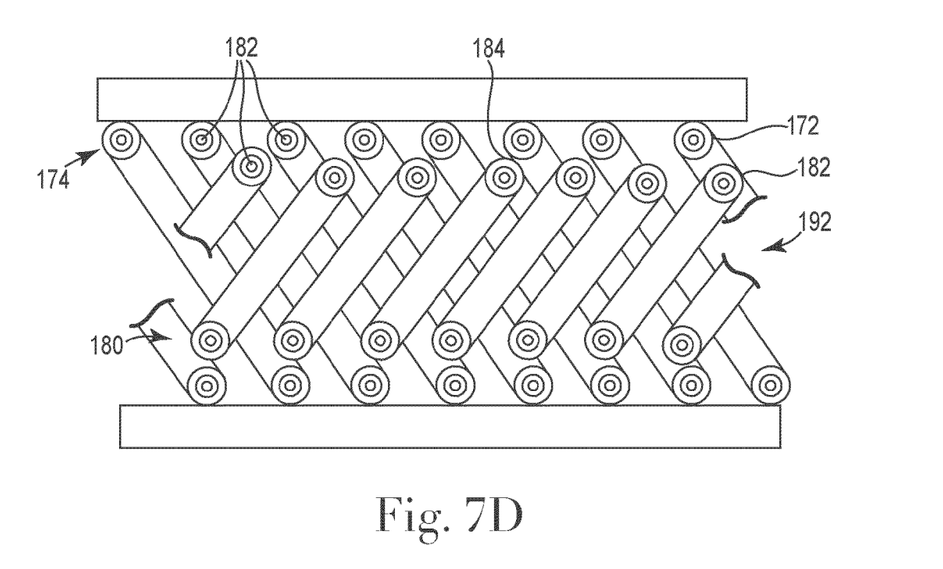

FIG. 7C is a cross sectional view conductor assembly 190 in which the electrical conductors 172 of the outer coil 174 are a plurality of insulated electrical conductors 182 each with a single conductive element and the electrical conductors 182 of the inner coil 180 are a plurality of un-insulated wires 176 surrounded by an insulating layer 178 in accordance with an embodiment of the present disclosure. FIG. 7D is a cross sectional view conductor assembly 192 in which the electrical conductors 172, 182 in both the inner and outer coils 180, 174 are a plurality of insulated electrical conductors 182 each with a single conductive element in accordance with an embodiment of the present disclosure. In both embodiments, the electrical conductors 172 in the outer coil 174 contact the electrical conductors 182 of the inner coil 180 at a plurality of interfaces 184.

Figure 8:
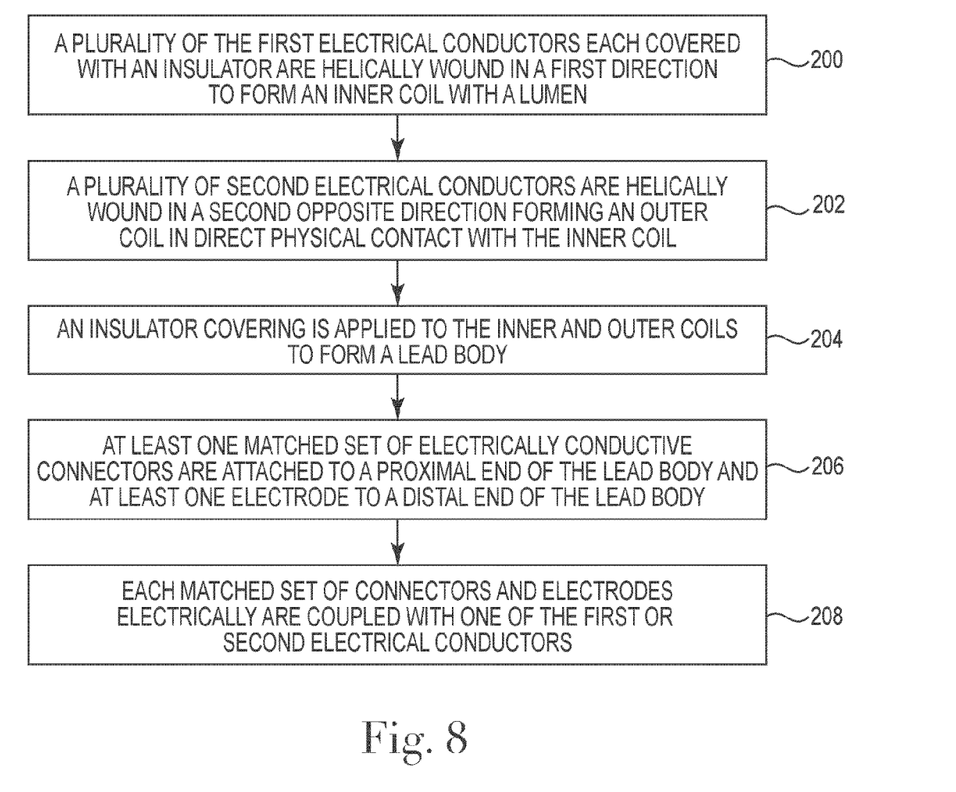
FIG. 8 is a flow chart of a method of making a stylet in accordance with an embodiment of the present disclosure.

FIG. 8 is a flow chart of a method of making a therapy delivery element adapted for at least partial insertion in a living body in accordance with an embodiment of the present disclosure. A plurality of the first electrical conductors each covered with an insulator are helically wound in a first direction to form an inner coil with a lumen (200). A plurality of second electrical conductors are helically wound in a second opposite direction forming an outer coil in direct physical contact with the inner coil. Each of the second electrical conductors includes a plurality of un-insulated wires twisted in a ropelike configuration around a central axis to form a cable covered with an insulator (202). An insulator covering is applied to the inner and outer coils to form a lead body (204). At least one electrically conductive connector is attached to a proximal end of the lead body and at least one electrode is attached to a distal end of the lead body (206). Each matched set of connectors and electrodes are electrically coupled with one of the first or second electrical conductors (208).

Figure 9:
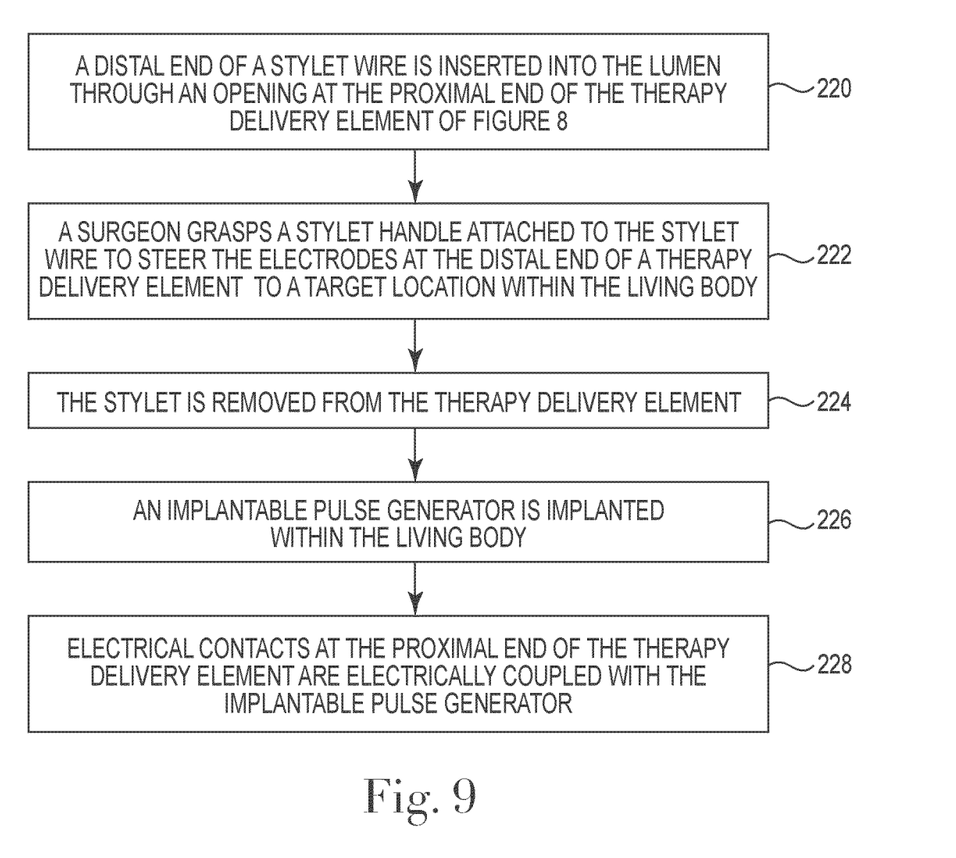
FIG. 9 is a flow chart of a method of implanting a neurostimulation system in accordance with an embodiment of the present disclosure.

FIG. 9 is a flow chart of a method of implanting a neurostimulation system in accordance with an embodiment of the present disclosure. A distal end of a stylet wire is inserted into the lumen through an opening at the proximal end of the therapy delivery element of FIG. 8 (220). The surgeon grasps a stylet handle attached to the stylet wire to steer the electrodes at the distal end of a therapy delivery element to a target location within the living body (222). The stylet is removed from the therapy delivery element (224). An implantable pulse generator is implanted within the living body (226). Electrical contacts at the proximal end of the therapy delivery element are electrically coupled with the implantable pulse generator (228).

Where a range of values is provided, it is understood that each intervening value, to the tenth of the unit of the lower limit unless the context clearly dictates otherwise, between the upper and lower limit of that range and any other stated or intervening value in that stated range is encompassed within this disclosure. The upper and lower limits of these smaller ranges which may independently be included in the smaller ranges is also encompassed within the disclosure, subject to any specifically excluded limit in the stated range. Where the stated range includes one or both of the limits, ranges excluding either both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the various methods and materials are now described. All patents and publications mentioned herein, including those cited in the Background of the application, are hereby incorporated by reference to disclose and described the methods and/or materials in connection with which the publications are cited.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Other embodiments are possible. Although the description above contains much specificity, these should not be construed as limiting the scope of the disclosure, but as merely providing illustrations of some of the presently preferred embodiments. It is also contemplated that various combinations or sub-combinations of the specific features and aspects of the embodiments may be made and still fall within the scope of this disclosure. It should be understood that various features and aspects of the disclosed embodiments can be combined with or substituted for one another in order to form varying modes disclosed. Thus, it is intended that the scope of at least some of the present disclosure should not be limited by the particular disclosed embodiments described above.

Thus the scope of this disclosure should be determined by the appended claims and their legal equivalents. Therefore, it will be appreciated that the scope of the present disclosure fully encompasses other embodiments which may become obvious to those skilled in the art, and that the scope of the present disclosure is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present disclosure, for it to be encompassed by the present claims. Furthermore, no element, component, or method step in the present disclosure is intended to be dedicated to the public regardless of whether the element, component, or method step is explicitly recited in the claims.

What is claimed is:

1. A biomedical conductor assembly adapted for at least partial insertion in a living body, the conductor assembly comprising:
    a plurality of first electrical conductors, each first electrical conductor being covered with an insulator;
    a plurality of second electrical conductors, at least one of the plurality of second electrical conductors including a plurality of un-insulated wires twisted in a ropelike configuration around a central axis to form a cable, each cable being covered with an insulator, the un-insulated wires being movable with respect to each other within the insulator, wherein the plurality of the first electrical conductors are helically wound in a first direction to form an inner coil with a lumen, and the plurality of the second electrical conductors are helically wound in a second opposite direction to form an outer coil around an outside of the inner coil and in direct physical contact with the inner coil, wherein the inner coil is substantially concentric with the outer coil; and
an insulator covering the inner and outer coils.

2. The conductor assembly of claim 1, wherein the inner coil is slidable relative to the outer coil within the conductor assembly.

3. The conductor assembly of claim 1, wherein at least one of the plurality of first electrical conductors includes a plurality of discrete insulated wires.

4. The conductor assembly of claim 1, wherein at least one of the plurality of first electrical conductors includes a plurality of un-insulated wires that are twisted in a ropelike configuration around a central axis to form a cable, wherein the cable is covered with an insulator.

5. The conductor assembly of claim 1, wherein at least one of the un-insulated wires of the at least one of the plurality of second electrical conductors includes a core of a first material surrounded by a covering of a second material.

6. The conductor assembly of claim 1, wherein at least one of the plurality of second electrical conductors includes a center wire of a homogeneous material and a plurality of un-insulated wires that are twisted in a ropelike configuration around the center wire.

7. The conductor assembly of claim 1, wherein at least one of the plurality of second electrical conductors includes a plurality of un-insulated wires wrapped around a center wire, wherein the center wire includes a breaking strength greater than a breaking strength of the un-insulated wires.

8. The conductor assembly of claim 1, wherein the inner coil includes four discrete insulated wires and the outer coil includes four or eight discrete insulated cables.

9. A biomedical conductor assembly adapted for at least partial insertion in a living body, the conductor assembly comprising:
a plurality of first electrical conductors that are each covered with an insulator and are helically wound in a first direction to form an inner coil with a lumen;
a plurality of second electrical conductors that are helically wound in a second opposite direction forming an outer coil around an outside of the inner coil and in direct physical contact with the inner coil, each of the second electrical conductors including a plurality of un-insulated wires twisted in a ropelike configuration around a central axis and covered with an insulator, wherein the inner coil is substantially concentric with the outer coil; and
an insulator covering the inner and outer coils.

10. A therapy delivery element comprising:
an elongated lead body including a proximal end and a distal end, the lead body including:
a plurality of first electrical conductors, each of the plurality of first electrical conductors being covered with an insulator and helically wound in a first direction to form an inner coil with a lumen;
a plurality of second electrical conductors, each of the plurality of second electrical conductors including a plurality of un-insulated wires twisted in a ropelike configuration around a central axis to form a plurality of cables, each cable being covered with an insulator and helically wound in a second opposite direction to form an outer coil around an outside of the inner coil and in direct physical contact with the inner coil, wherein the inner coil is substantially concentric with the outer coil; and
an insulator covering the inner and outer coils.

11. The therapy delivery element of claim 10, comprising a stylet wire including:
a distal end configured to be inserted into the lumen of the inner coil through an opening at the proximal end of the lead body; and
a proximal end attached to a stylet handle.

12. A neurostimulation system comprising:
an implantable pulse generator; and
a therapy delivery element including:
an elongated lead body including a proximal end and a distal end, the distal end including at least one electrode, the lead body including:
a plurality of first electrical conductors, each of the plurality of first electrical conductors being covered with an insulator and helically wound in a first direction to form an inner coil with a lumen;
a plurality of second electrical conductors, each of the plurality of second electrical conductors including a plurality of un-insulated wires twisted in a ropelike configuration around a central axis to form a plurality of cables, each cable being covered with an insulator and helically wound in a second opposite direction to form an outer coil around an outside of the inner coil and in direct physical contact with the inner coil, wherein the inner coil is substantially concentric with the outer coil; and
an insulator covering the inner and outer coils;
an electrically conductive connector operatively associated with the proximal end of the lead body, wherein the connector and the at least one electrode are electrically coupled with one of the plurality of first electrical conductors or the plurality of second electrical conductors, wherein the connector is configured to electrically couple with the implantable pulse generator; and
a stylet wire including:
a distal end configured to be inserted into the lumen of the inner coil through an opening at the proximal end of the lead body; and
a proximal end attached to a stylet handle.

13. A method of making a therapy delivery element adapted for at least partial insertion in a living body, the method comprising:
helically winding a plurality of first electrical conductors in a first direction to form an inner coil with a lumen, each of the plurality of first electrical conductors being covered with an insulator;
helically winding a plurality of second electrical conductors in a second opposite direction to form an outer coil around an outside of the inner coil and in direct physical contact with the inner coil, each of the second electrical conductors including a plurality of un-insulated wires twisted in a ropelike configuration around a central axis to form a plurality of cables, each cable being covered with an insulator, wherein the inner coil is substantially concentric with the outer coil;
applying an insulator covering to the inner and outer coils to form a lead body;
attaching at least one electrically conductive connector to a proximal end of the lead body; and
attaching at least one electrode to a distal end of the lead body, wherein the at least one electrode and the at least one connector are electrically coupled with one of the plurality of first electrical conductors or the plurality of second electrical conductors.

14. The method of claim 13, wherein the inner coil is slidable relative to the outer coil within the conductor assembly.

15. The method of claim 13, wherein at least one of the plurality of first electrical conductors includes a plurality of discrete insulated wires.

16. The method of claim 13, wherein at least one of the plurality of first electrical conductors includes a plurality of un-insulated wires twisted in a ropelike configuration around a central axis to form a cable, the cable being covered with an insulator, the un-insulated wires being movable with respect to each other within the insulator.

17. The method of claim 13, wherein at least one of the plurality of second electrical conductors includes a plurality of un-insulated wires wrapped around a center wire, wherein the center wire includes a breaking strength greater than a breaking strength of the un-insulated wires.

18. The method of claim 13, wherein the inner coil includes four discrete insulated wires and the outer coil includes four or eight discrete insulated cables.

19. The method of claim 13, comprising inserting a distal end of a stylet wire into the lumen of the inner coil through an opening at the proximal end of the therapy delivery element.

20. A method of implanting a neurostimulation system comprising:
 steering, using the stylet wire, the distal end of the therapy delivery element of claim 11 to a target location within the living body;
 removing the stylet from the therapy delivery element;
 implanting an implantable pulse generator within the living body; and
 electrically coupling the electrical contacts at the proximal end of the therapy delivery element with the implantable pulse generator.

* * * * *